United States Patent [19]

Meyerhoff et al.

[11] Patent Number: 6,159,958
[45] Date of Patent: Dec. 12, 2000

[54] TREATMENT OR PROPHYLAXIS OF RETINAL PATHOLOGY AND SPINAL CORD INJURY

[75] Inventors: James M. Meyerhoff, Silver Spring, Md.; Henry D. Hacker, Temple, Tex.; Joseph B. Long, Clarksville, Md.

[73] Assignee: The United States of America as represented by the Secretary of the Army, Washington, D.C.

[21] Appl. No.: 09/133,805

[22] Filed: Aug. 13, 1998

Related U.S. Application Data

[60] Provisional application No. 60/055,613, Aug. 14, 1997, and provisional application No. 60/055,614, Aug. 14, 1997.

[51] Int. Cl.⁷ ............................ A67K 31/66; A67K 31/22
[52] U.S. Cl. ........................... 514/148; 514/546; 514/912
[58] Field of Search .................................. 514/148, 546, 514/912

[56] References Cited

U.S. PATENT DOCUMENTS 5,597,809  1/1997  Dreyer ........................................ 514/37

*Primary Examiner*—Zohreh Fay
*Attorney, Agent, or Firm*—Elizabeth Arwine; Charles H. Harris

[57] ABSTRACT

Compositions containing 2-(phosphonomethyl)-pentanedioic acid (PMPA) and α and β N-acetyl-aspartyl-glutamate (NAAG) are appropriate means for treatment of neuronal tissue injury that may result from such factors as injury, toxicity, hypoxia or ischemia (a frequent cause of hypoxia). Target tissues include the brain, spinal cord and retina.

7 Claims, No Drawings

TREATMENT OR PROPHYLAXIS OF RETINAL PATHOLOGY AND SPINAL CORD INJURY

This application claims benefit to provisional application Ser. No. 60/055,613 filed Aug. 14, 1997 which claims benefit to provisional application Ser. No. 60/055,614 filed Aug. 14, 1997.

FIELD OF THE INVENTION

This invention relates to the use of 2-(phosphonomethyl) pentanedioic acid (PMPA) and α and β N-acetyl-aspartyl-glutamate (NAAG) for treatment of neuronal tissue injury that may result from such factors as injury, toxicity, hypoxia or ischemia (a frequent cause of hypoxia). Target tissues include the brain, spinal cord and retina.

BACKGROUND OF THE INVENTION

It is known that the neurotransmitter, N-Acetyl-aspartyl-glutamate (NAAG), which is found throughout the nervous system, is enzymatically converted to the potentially exitotoxic neurotransmitter, glutamate, by the enzyme α-linked acidic dipeptidase (NAALADase), also known as NAAG-hydrolyzing enzyme, in both normal and in pathophysiological conditions of the neurological system. (A new name was recently proposed for NAALADase: glutamate carboxypeptidase II.) Under current practice, drugs are used to block glutamate at its receptor "downstream". However, there has not previously been an adequate method for blocking the enzymatic formation of glutamate from an immediate precursor, NAAG.

It is believed that NAAG is released in response to neuronal trauma/ischemic injury, and is then hydrolyzed to form glutamic acid. Because NAAG has only a fraction of the excitatory potency of glutamic acid, the concentration of NAAG required to be neurotoxic might be 100-fold the toxic concentration of glutamic acid.

At present, spinal injury, whether arising from trauma or disease, disables many Americans of all ages. There has previously been no really effective therapeutic agent for use in treatment of such CNS injuries. Injuries such as those arising from penetrating injuries, exposure to blast, blunt trauma, falls and vehicular accidents as well as spinal cord and brain injury secondary to decompression sickness are examples of instances when use of PMPA, α-NAAG or β-NAAG in accord with the teachings of this disclosure would be appropriate. Any damage which results in hypoxia, including ischemia and toxicity, can cause severe damage to the neuronal tissue.

A neuronal tissue that is particularly subject to damage arising from hypoxia, ischemia, exposure to toxins or any other causes of degeneration is the retina.

The leading causes of blindness in the United States include age-related macular degeneration (AMD), diabetic retinopathy, glaucoma and cataracts. The prevalence of diabetes in North America is expected to reach almost 17 million by the year 2000. In cases of insulin-dependent diabetes mellitus (IDDM) with onset before age 30, the average prevalence of proliferative retinopathy is estimated at 23%. In the case of IDDM of more than 30 years duration, however the incidence of proliferative retinopathy rises to 70%. Proliferative retinopathy is the leading cause of new cases of blindness in the U.S., accounting for 12% of new cases annually.

The prevalence of AMD increases from over 2% in the age group 60–64 years to over 25% in the 75–80 year age group. It is estimated that the prevalence of glaucoma in the United States will be 2.9 million by the year 2000, and that over 130,000 will have been blinded by this disease.

At present, eye drops are available for treating vernal conjunctivitis containing both α- and β-NAAG. β-NAAG is a very weak NAALADase inhibitor that also has been found to act as an agonist. (ANAAG is also an agonist.) Thus, β-NAAG is not a specific NAALADase inhibitor. However, neither α-NAAG nor β-NAAG were previously known to have use in treating or preventing damage to the retina or other neuronal tissue.

SUMMARY OF THE INVENTION

The instant invention is related to use of PMPA and α-NAAG and β-NAAG to prevent and treat conditions arising from exposure of neuronal tissue to toxins, injury, ischemia and hypoxia.

DETAILED DESCRIPTION OF THE INVENTION

It is now found that it is possible to inhibit the enzyme NAALADase, thereby blocking enzymatic conversion of NAAG to glutamate using PMPA. This approach is useful because blocking a metabolic source of glutamate may require less drug. Furthermore, previously known glutamate receptor blockers have unacceptable side effects.

The value of NAAG on the CNS was also studied. Hydrolysis of NAAG by N-acetylated α-linked acidic dipeptase (NAALADase) liberates the more potent excitatory amino acid neurotransmitter, glutamate (GLU). Consequently, NAAG has been regarded as a storage form of synaptic GLU and NAALADase has been proposed to modulate neuronal excitability by regulating the synaptic availability of GLU. NAAG has also been proposed to inhibit GLU release through activation of presynaptic mGluR3 receptors, and at low concentrations it has been shown to antagonize NMDA receptor-mediated responses.

It was found that it is possible to prevent toxicity or treat damage to neuronal tissue, including the spinal cord Such damage may, for example arise from hypoxia in the CNS. Hence, traumatic injuries and diseases may be treated using PMPA and analogues which inhibit NAALADase may be used for treatment of such diseases. Injuries such as those arising from penetrating injuries, exposure to blast, blunt trauma, falls and vehicular accidents as well as spinal cord and brain injury secondary to decompression sickness are examples of instances when use of PMPA, α-NAAG and β-NAAG in accord with the teachings of this disclosure would be appropriate.

Studies in culture showed that PMPA protected spinal neurons from hypoxic injury in vitro. Furthermore, in studying the effect of PMPA, lumbar subarachnoid injections of dynorphin A (DYN) were administered to rats causing ischemic injury and paralysis that is mediated through excitatory amino acid receptors. The DYN was co-administered with PMPA at dosage of 0.4, 0.8 and 4 μm. It was found that animals who received PMPA with the DYN showed evidence of significant protection from dynorphin-induced ischemia.

In order to study the effect of NAAG on the CNS, an accepted injury model was used to evaluate the pharmacological effects of NAAG (0.25–4 μmoles), specifically examining its effect on recovery of the persistent HL motor deficits elicited by L4–L5 subarachnoid injection of 10 ηmoles of dynorphine A (DYN). Spinal subarachnoid injections of NAAG alone did not alter HL motor function. When co-administered with DYN, NAAG caused significant dose-dependent improvements in motor scores by 24 hours post-injection. (p<0.05, Kruskal-Wallis). Paralysis was still acutely evident after NAAG co-treatment. However, NAAG-induced improvements in recovery became increasingly apparent between 2 and 24 hours post-injection. The non-hydrolyzable analog β-NAAG also significantly improved recovery of HL motor function, indicating that this effect was not secondary to cleavage of NAAG into N-acetylaspartate and GLU.

The results indicate that NAAG has protective effects in instances of exitotoxic spinal cord injury that are likely to be mediated through NMDA receptors. Another form of injury for which prophylactic treatment is needed is occasioned by exposure of neuronal tissue to irradiation such as that which occurs in the spinal cord when irradiation is targeted for treatment of malignancies of the abdomen or in the retina when whole-head irradiation is administered for malignancies of the brain.

Dosage of NAAG and PMPA are essentially the same, and will, of course, depend on the age, size and condition of the patient as well as on the mode of administration.

For purposes of obtaining beneficial effects on the CNS, the agents of the invention can be delivered by any means which allows the active agent to contact the injured tissue. In the case of the spinal cord, the agents may be administered intrathecally or by caudal drip. Carriers which are appropriate are those which are basically non-irritating such as buffered saline which may contain glucose and other active agents such as antibiotics and anti-inflammatory agents. The concentration of PMPA is usually 0.05% to 6%. For example, a solution containing 0.5% PMPA in 5% glucose in phosphate buffered saline may be administered intrathecally. Compositions containing PMPA may also be administered into the cisterna magna.

In addition to providing benefit for protection of the brain and spinal cord, PMPA, α-NAAG and β-NAAG may be used to prevent toxic damage to the retina, including damage arising from hypoxia in the retina. Hence, diseases which may be treated using PMPA and analogues which inhibit NAALADase may be used for treatment of such diseases as glaucoma, damage from exposure to laser, blast over-pressure, blunt or penetrating injuries to the eye and photocoagulation such as that used in treatment of macular degeneration or diabetic retinopathy.

Other diseases which affect the retinal vasculature such as lupus erythematosus and temporal arteritis are also responsible for loss of sight. It appears a therapeutic window exists during the disease process when agents that reduce glutamate activity at its receptor sites can rescue neurons from injury.

Exposure of the retina to laser energy, whether therapeutic or accidental, results in formation of scotoma and visual impairment. Even after therapeutic exposures, there may be immediate and progressive visual impairment due to destruction of normal retinal cellular elements with subsequent spread of injury to adjacent retinal tissue. Compositions containing PMPA may be administered prophylactically before expected exposure to laser treatment or immediately after accidental exposure.

The agents of the invention can be delivered by any means which allows the active agent to contact the retina, including intraocular injection and administration of eye drops containing carriers such as polyvinyl alcohol. Carriers which are appropriate are those which are basically non-irritating such as buffered saline containing 5% polyvinyl alcohol of such weight (number) as to be soluble in water. The PMPA may also be provided as a salve or ointment. (Higher concentrations of polyvinyl alcohol will be useful in preparation of ointments.) The concentration of PMPA is usually 0.05% to 6%. For example, a solution containing 0.5% PMPA in phosphate buffered saline containing 5% polyvinyl alcohol may be administered as drops at about 1–5 drops per dosing.

It has now been found that α-NAAG and β-NAAG also provide neuroprotective effects. Without relying on any particular theory for novelty, it is believed that these beneficial effects may result from competition for the glutamate receptor by α- and β-NAAG acting as a partial agonist at the N-methyl,D-aspartate (NMDA) receptor complex. It is also possible that the α-NAAG and β-Naag are acting as agonists at the presynaptic mGluR3.

To model ischemias, sodium cyanide (NaCN) to inhibit oxidative metabolism and 2-deoxyglucose (2-DG) to inhibit glycolysis were used. Dissociated rabbit retina cells were studied to evaluate the potential neuroprotective effects of α- and β-NAAG. It was found that metabolic inhibition with NaCN/2-DG for 1 hour caused 50% toxicity when viability was assessed using the tetrazolium dye assay for succinate dehydrogenase activity. Co-treatment with α-NAAG resulted in dose-dependent protection of up to 55% (p<0.0005, T-test). When the unhydrolysable β-NAAG was employed, a dose-dependent protection of up to 37% was observed (p<0.001, T-test).

The active agents of the invention are readily available commercially. Compositions containing PMPA and α- and β-NAAG may be administered for treatment of conditions of the retina by such means as eye drops or by injection. Appropriate carriers include saline, glucose (5% or 10% being more usual) in half normal saline, and buffered saline, etc. Compositions may also contain other agents used as carriers such as dimethylsulfoxide (DMSO).

For intraocular administration, as an example, a 0.05% solution of PMPA in saline may be injected into the eye.

Compositions for use in the method of this invention may contain, in addition to PMPA, other active agents such as anti-inflammatory agents, antibiotics, alkaloids, anesthetics and analgesics.

The dosage administered will depend on the condition, size and age of the patient. In general, dosage of 0.0001/Kg to 1 mg/Kg for PMPA, α-NAAG or β-NAAG will be appropriate, with larger animals such as man receiving about 0.0001 to 0.05 mg/Kg and smaller animals receiving larger dosage relative to weight.

Compositions for use in the method of this invention may contain, in addition to PMPA, other active agents such as anti-inflammatory agents, antibiotics, anesthetics and analgesics.

Chronic depot delivery systems known in the art may be used to deliver the active agents. For purposes of treating retinal diseases, the active agents may also be administered intraocularly such as, for example, by intravitreal means.

Example 1:

A composition for administration by injection (including intrathecal injection) is prepared by adding 3 mg PMPA to 3 ml DMSO. To this is added sufficient 5% glucose in half-normal saline to make 100 ml solution.

Example 2:

A composition is prepared for use as eye drops. Six mg of β-NAAG is added to 3 ml DMSO. To this is then added sufficient saline to make 100 ml of solution.

Example 3:

A composition is prepared for intrathecal injection by adding sufficient 10% glucose in half-normal saline to 3 mg of α-NAAG to provide 100 ml of solution.

It is urged that the above examples are provided for purposes of general instruction and are not to be construed as in any way limiting the scope of the invention.

What we claim is:

1. A method of treating or protecting against neurological damage in a subject in need thereof comprising administration of a composition of matter comprising a glutamate formation inhibiting effective amount of an active agent chosen from 1-(phosphonomethyl) pentanedioic acid, alpha N-acetyl-aspartyl-glutamate, and beta N-acetyl-aspartyl-glutamate in a pharmaceutically acceptable carrier.

2. A method of claim 1 wherein the neurological damage arises from trauma, vertebral disease or decompression sickness.

3. A method of claim 1 wherein the neuronal tissue requiring treatment or protection is retinal tissue.

4. A method of claim 3 wherein the composition is administered in the form of eye drops.

5. A method of claim 1 wherein composition contains 0.5% to 6% PMPA, α-NAAG or β-NAAG.

6. A method of claim 3 wherein the composition contains 0.5% to 6% PMPA.

7. A method of treating or protecting against damage to the retinal tissue to a subject in need thereof by administration of a composition containing a retinal protecting or retinal damage treating effective amount of 2-(phosphonomethyl) pentanedioic acid in (PMPA) a pharmaceutically acceptable carrier.

* * * * *